Figure 1:
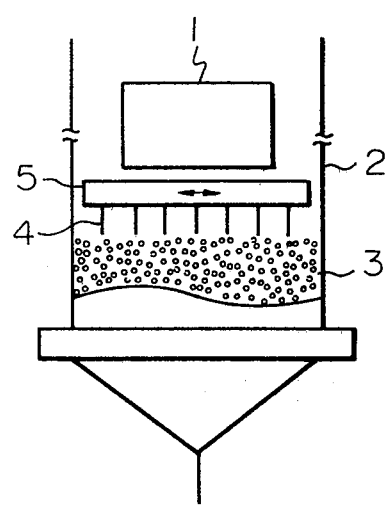

United States Patent [19]

Tanouchi et al.

[11] 4,450,082
[45] May 22, 1984

[54] METHOD FOR OBTAINING UNIFORM STREAM IN ADSORPTION COLUMN

[75] Inventors: Masatoshi Tanouchi, Arcadia, Calif.; Yoshiyuki Asahina, Nobeoka, Japan

[73] Assignee: Asahi Kasei Kogyo Kabushiki Kaisha, Osaka, Japan

[21] Appl. No.: 383,693

[22] Filed: Jun. 1, 1982

[30] Foreign Application Priority Data

| Jun. 11, 1981 | [JP] | Japan | 56-88812 |
| Jun. 11, 1981 | [JP] | Japan | 56-88813 |
| Oct. 29, 1981 | [JP] | Japan | 56-172096 |
| Nov. 2, 1981 | [JP] | Japan | 56-174434 |

[51] Int. Cl.³ .......................................... B01D 15/00
[52] U.S. Cl. ................................. 210/660; 210/656; 210/807; 210/290; 55/74; 55/386
[58] Field of Search .............. 210/656, 807, 280, 283, 210/290, 291, 198.2, 660; 55/386, 74

[56] References Cited

U.S. PATENT DOCUMENTS

| 2,000,696 | 5/1935 | Friend et al. | 210/291 X |
| 3,382,983 | 5/1968 | Stewart | 210/290 X |
| 3,422,605 | 1/1969 | Crowley | 55/386 |
| 4,259,186 | 3/1981 | Boeing | 55/386 |

FOREIGN PATENT DOCUMENTS 47-13043  4/1972  Japan.
52-15029  2/1977  Japan.
52-15030  2/1977  Japan.
54-1716   1/1979  Japan.

OTHER PUBLICATIONS

Introduction to Modern Liquid Chromatography by Snyder et al., See pp. 178–184, John Wiley & Sons of New York, 1974.
Gas Chromatography by Szepesy, See p. 205, CRC Press of Cleveland, 1970.
S. Hiranaka "Haikan (Piping) Gijutsu (Technique)", pp. 59–65, May 1979.
N. Standish and G. D. Bull Chem. Eng. Sci., 36, 774–776 (1981).

Primary Examiner—John Adee
Attorney, Agent, or Firm—Armstrong, Nikaido, Marmelstein & Kubovcik

[57] ABSTRACT

A method for obtaining uniform stream in an adsorption column is disclosed. This method uses an adsorption column having at least one single-flow passage in which the ratio of the inner diameter of the column to the average particle size of a packing to be packed in the adsorption column is at least 20, and comprises classifying the packing to be packed in the adsorption column and packing the fractions of the packing into the adsorption column in the order of particle size. Thus, a desired substance or substances contained in a mixture can be adsorbed and then separated as a uniform stream in an adsorption column.

11 Claims, 13 Drawing Figures

$$\sigma^2 = \frac{\beta^2}{8}$$

METHOD FOR OBTAINING UNIFORM STREAM IN ADSORPTION COLUMN

The present invention relates to a technique for performing a separating operation at a high efficiency in an adsorption column. More particularly, the present invention relates to a technique for preventing channeling of a fluid in an adsorption column to obtain a stream uniform in the radial direction of the cross section of the column and to facilitate scale-up of the adsorption column.

Fixed bed type adsorption columns packed with solid adsorbents such as ion exchange resins and zeolites have recently been actually utilized on an industrial scale for selectively adsorbing and separating special substances from mixtures. For example, adsorption columns packed with ion exchange resins are used for the separation of fructose and glucose, the separation of metal ions such as rare earth metal ions and the separation of amino acids, and adsorption columns packed with zeolites are used for the separation of n-paraffins, the separation of n-olefins, the separation of xylene isomers, cymene isomers and diethylbenzene isomers, the separation of cyclohexane and cyclohexene and the separation of fructose and glucose.

It is well-known that a so-called high-speed liquid chromatography method using high-capacity porous particles such as Zipak ®, Porasil ®, Sil ® and Zorbax ® has rapidly been developed as an effective means for the separation of organic substances. These adsorbents are used in the state packed in fixed bed type adsorption columns.

The present invention may be applied to any of the fixed bed type adsorption columns packed with the foregoing adsorbents, but especially good results can be obtained when the present invention is applied to a method for separating p-xylene from a mixture of xylene isomers in an adsorption column packed with a zeolite adsorbent.

In the actual utilization of these fixed bed type adsorption columns, one of important problems is how to obtain and maintain a uniform stream in the radial direction of the adsorption column. When a uniform stream cannot be obtained or maintained in the radial direction of the adsorption column, that is, when channeling occurs in a fluid, the flow speed distribution, concentration distribution and temperature distribution become uneven in the radial direction of the packed layer, and in this case, the utilization efficiency of the volume of the packed layer is much lower than in the case where a uniform stream is obtained and maintained and a larger volume is necessary to obtain the same separation effect, resulting, in economical disadvantages. Furthermore, in the fixed bed type adsorption column, the concentration distribution generated in the radial direction is reduced in the outlet due to the gathering and hence, bands differing in the concentration are mingled in the axial direction, with the result that separated component bands are mingled again and the separation efficiency is drastically reduced. Also in an ordinary fixed bed type reactor, a uniform stream is required so as to ensure effective utilization of the packed volume and to reduce the temperature distribution. In an adsorption column, however, the separation efficiency is significantly influenced by mixing of a substance to be adsorbed with an adsorbent or mixing of separated components, and the effective volume is reduced by this mixing or the process is rendered substantially impossible by this mixing. Accordingly, in the case of an adsorption column, the maintenance of a uniform stream in the radial direction is more strictly required than in case of other ordinary packed columns, and scale-up of the column by increase of the radius of the column is very difficult.

Namely, in the actual utilization of an adsorption column, it is one of important problems to obtain and maintain a uniform distribution of the fluid along the radial direction in the column, solution of which is an object of the present invention.

In order to obtain and maintain a uniform distribution of a fluid in the radial direction in a fixed bed type adsorption column, it is important that the following two conditions are satisfied.

(A) The structure of the packed zone should be as uniform as possible in the radial direction of the column.

(B) Distribution of the fluid to the packed zone and gathering of the fluid from the packed zone should be performed as uniformly as possible.

There have been proposed various methods as means for satisfying the condition (A). For example, there can be mentioned a so-called "Sock" method in which a hopper equipped with a hose extended to the surface of a packing charged into a packing vessel is employed, the packing is introduced into the hopper and hose and the hose is gradually drawn up to discharge the packing from the bottom portion of the hose. According to this method, occurrence of a channeling phenomenon which is one of causes of formation of a non-uniform packing structure, is considerably prevented. However, the obtained pack density is low and the formed packing structure is readily changed during the operation. Moreover, in this method, since a force overcoming the frictional force generated among particles of the packing is not applied to the packing, formation of large voids among particles of the packing, that is, so-called "arching", cannot be prevented, and when the packing has a broad particle size distribution range, microscopically speaking, segregation is caused to result in channeling and satisfactory adsorption-separation can not be attained.

Japanese Patent Publication No. 6990/79 teaches that according to a packing method disclosed therein, a uniform packing structure having a high pack density can be attained. This packing method, however, is directed mainly to packing of a packing in a fixed bed type reactor, and if this method is applied to a fixed bed type reactor, the uniformity and the density of packing is improved over the known Sock method. Since the uniformity required for a fixed bed type adsorption column is much higher than the uniformity required for a fixed bed type reactor as pointed out hereinbefore, even if this method is applied to the adsorption column, no necessary uniformity can be attained.

In a small-scale column such as a column used in the case of a liquid chromatography analytic apparatus, a packing having a very narrow particle size distribution range is used in some case. Indeed, if a packing having a narrow particle size distribution range is used, a uniform packing structure can be obtained considerably easily. However, if such packing is used in the case of a large-scale apparatus, a large quantity of the packing should be subjected to classification and the utilization efficiency (yield) of the packing is drastically reduced. Accordingly, the packing method using a packing having a narrow particle size distribution range is not preferred from the practical viewpoint.

We made researches with a view to developing a packing method which can be applied to a packed column for adsorption and separation, in which all of the foregoing defects of the conventional methods can be eliminated, and as a result, we have now completed the present invention described below.

Accordingly, an object of the present invention is to eliminate the foregoing defects of the conventional methods and to provide a method for obtaining a uniform stream in an adsorption column for adsorbing and separating a substance to be separated from a mixture.

Other objects and advantages of the present invention will be apparent from the description set forth hereinbelow.

In accordance with the present invention, there is provided a method for obtaining a uniform stream in an adsorption column for adsorbing and separating a substance from a mixture, said adsorption column having at least one single-flow passage in which the ratio of the inner diameter of the column to the average particle size of a packing to be packed in the adsorption column is at least 20 (or 20:1), said method comprising classifying the packing to be packed in the adsorption column and packing the fractions of the packing into the adsorption column in the order of particle size.

The present invention will now be illustrated in detail with reference to the accompanying drawings.

FIG. 1 illustrates an embodiment in which the filler is packed under vibration generated by vibrators inserted into the column, wherein reference numerals 1, 2, 3, 4 and 5 represent a vibrating device, an adsorption column, a packing, a vibrator and a vibrating plate, respectively.

Figure 2:
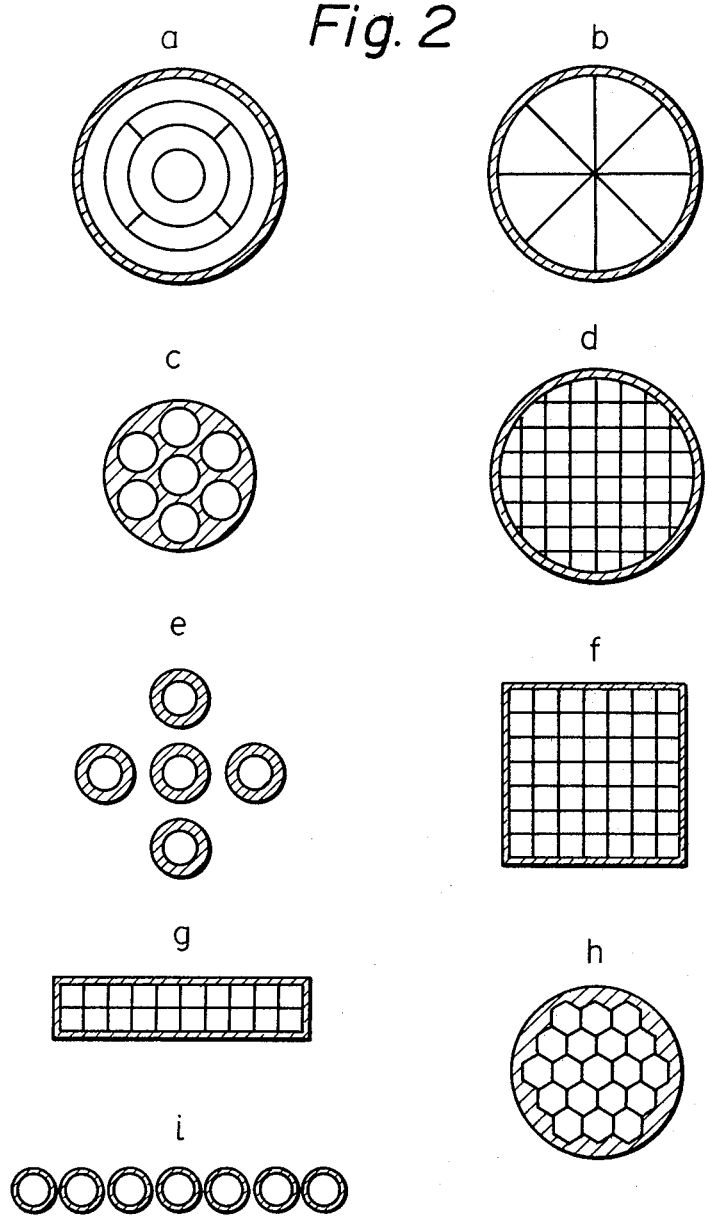
Figure 3A:
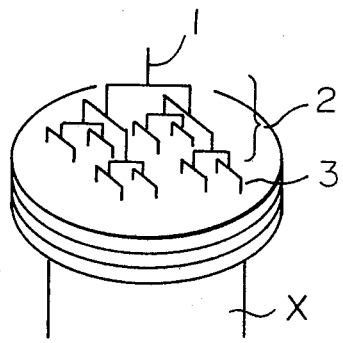
Figure 3B:
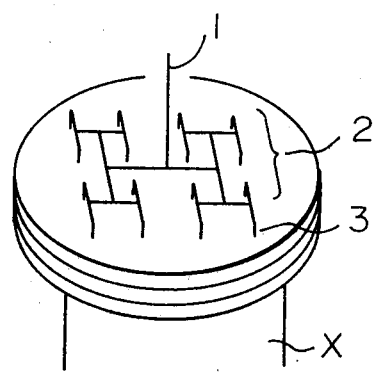
Figure 3C:
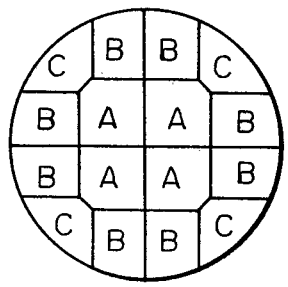
Figure 3D:
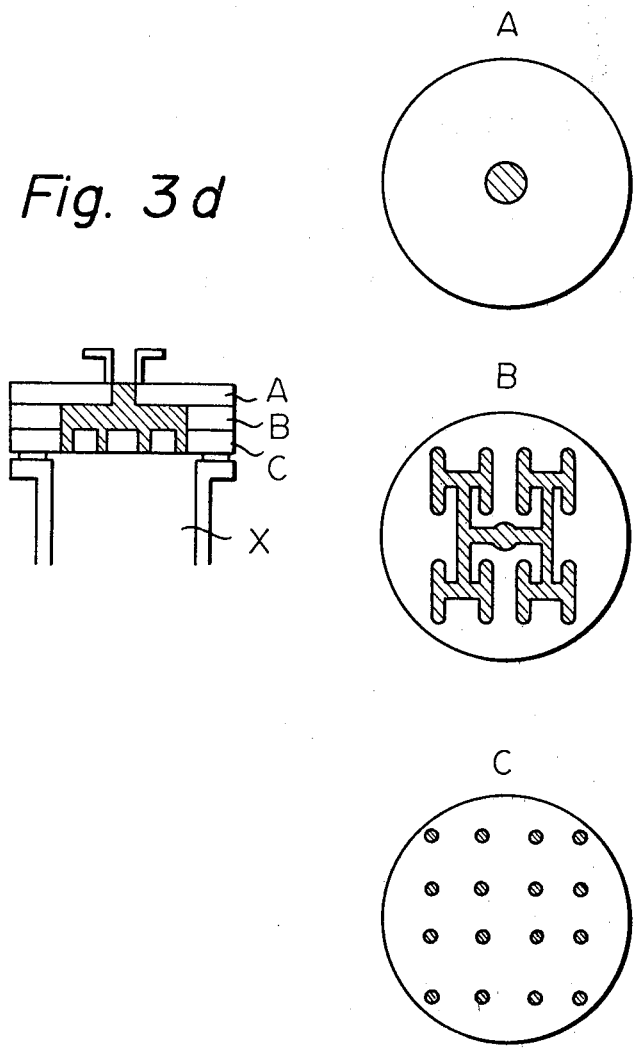
Figure 3E:
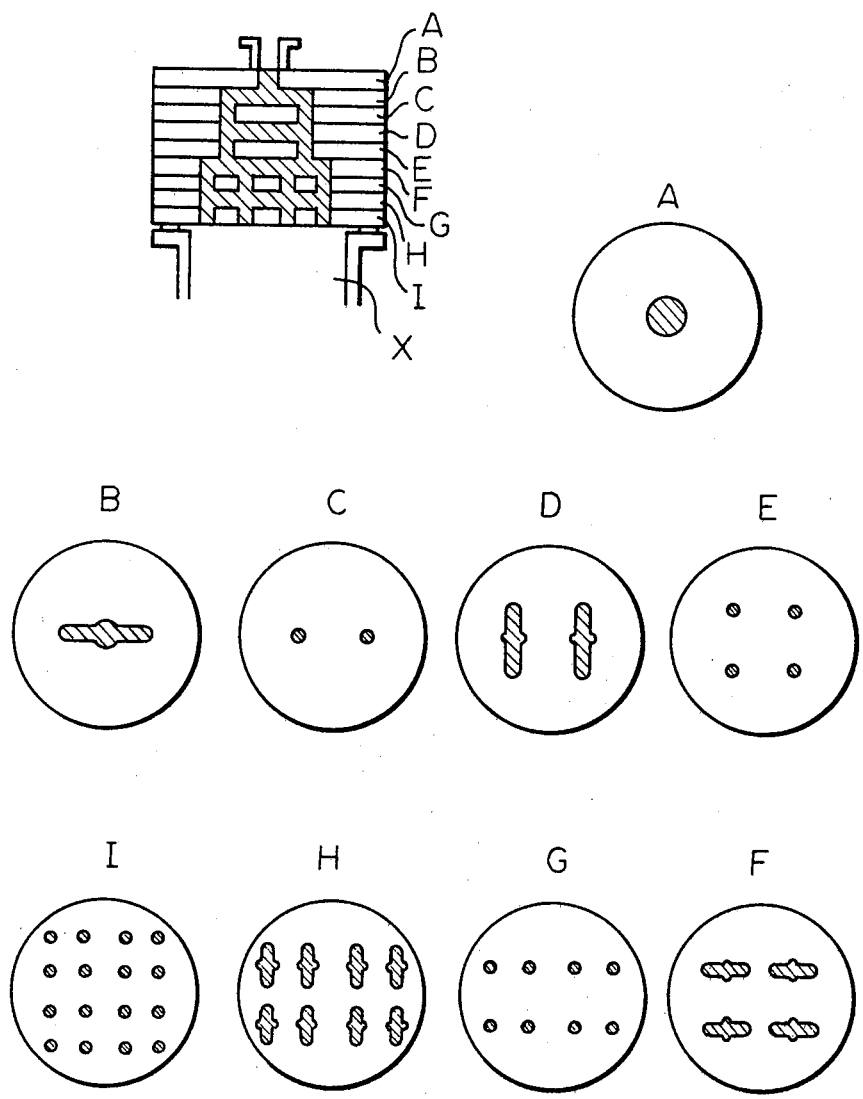
Figure 3F:
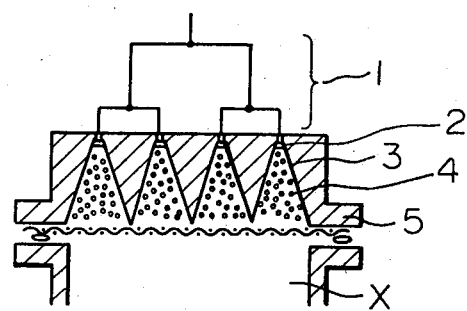

FIGS. 2-a through 2-i are diagrams showing a section in the flow direction and illustrate examples of the multiple flow-passage type of construction.

FIGS. 3-a through 3-f show examples of the distributing and gathering zones. FIG. 3-a shows a typical instance of repetition of divisions into 2 branches which is constructed by pipes according to the present invention. In FIG. 3-a, reference numerals 1, 2 and 3 represent a junction, a branch and a final branch end (opening), respectively, and symbol X represents a packed zone.

FIG. 3-b shows a modification of the construction shown in FIG. 3-a, branches are formed on one plane by pipes by repetition of division into two branches. In FIG. 3-b, reference numerals 1, 2 and 3 represent a junction, a branch and a final branch end (opening), respectively, and symbol X represents a packed zone.

FIG. 3-c shows an example in which the surface area of the packed layer is divided into three kinds of sections A, B and C which are equal in the area and it is preferred that the final branch end be located at the centroid in each section.

FIG. 3-d shows an example of the distributing or gathering device according to the present invention, in which branches by repetition of division into two branches are formed on a plate on the same plane and which consists of three plates A, B and C having different openings, which are combined together. In FIG. 3-d, symbol X represents the packed zone.

FIG. 3-e shows a modification of the distributing or gathering device shown in FIG. 3-d, in which branches of one stage are formed on a plate on the same plane and which consists of nine plates A through I having different openings, which are combined together. In FIG. 3-e, symbol X represents a packed zone.

Figure 4A:
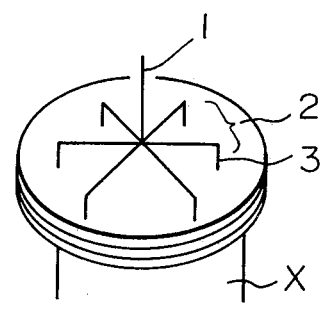
Figure 4B:
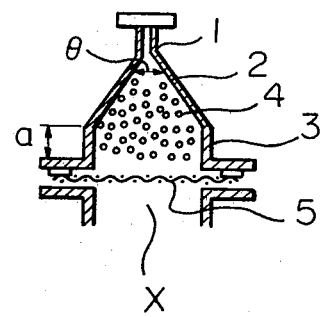

FIG. 3-f illustrates an example in which conical reducers having bottom faces covering the entire surface of the packed zone are arranged between the packed zone and the distributing or gathering device of FIG. 3-a according to the present invention. In FIG. 3-f, reference numeral 1 represents a branch of the distributing or gathering device shown in FIG. 3-a, reference numeral 4 represents beads, reference numerals 2 and 5 represent metal wire nets, reference numeral 3 represents a conical reducer, and symbol X represents a packed zone;

FIG. 4-a shows an example of the conventional distributing or gathering device in which reference numerals 1, 2 and 3 represent a junction, a branch and a branch end, respectively, and symbol X represents a packed zone.

FIG. 4-b shows another example of the conventional distributing or gathering apparatus, in which reference numeral 2 represents a conical reducer, reference numeral 3 represents a straight portion, reference numeral 4 represents beads, reference numerals 1 and 5 represent metal wire nets, and symbol X represents a packed zone.

Figure 5:
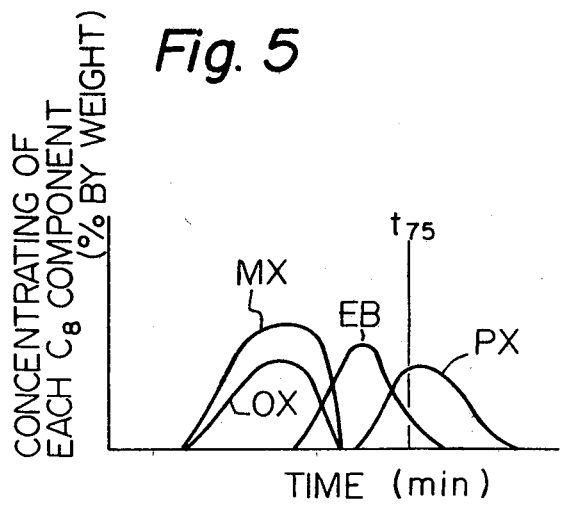

FIG. 5 is an example of the chromatogram at the column outlet, which is obtained when p-xylene is selectively adsorbed and separated from a mixture of xylene isomers in an adsorption column constructed according to the present invention. In FIG. 5, MX represents m-xylene, OX represents o-xylene, EB represents ethylbenzene, PX stands for p-xylene, $t_{75}$ represents the position (min) of cutting the chromatographical band for obtaining PX having a purity of 75%, which PX has been accumulated from the rear end (the hatched portion indicates the amount of PX that can be obtained by cutting PX from other components at $t_{75}$), and $R_{75}$ represents the weight ratio (% by weight) of the recovered amount of PX to the amount of PX contained in the starting mixture.

Figure 6:
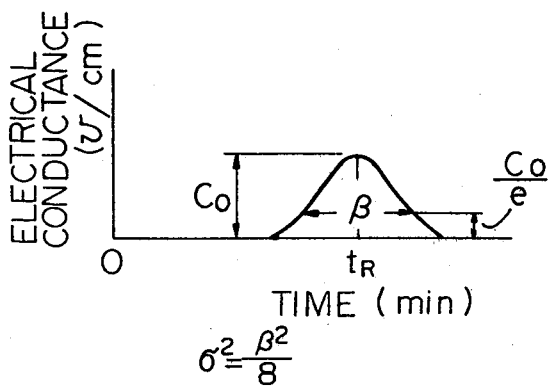

FIG. 6 shows an example of the KCl pulse response curve. In the Examples of the present invention, because of the necessity of the precision, a pulse response curve as shown in FIG. 6 is converted from the actually measured step response curve to determine the degree of channeling. In FIG. 6, symbol Co represents the height ($\mho$/cm) of the maximum peak obtained by the conversion, symbol e represents the base (=2.718) of the natural logarithm, symbol $\beta$ represents the peak width (min) at the height of Co/e, and $\sigma_2$ represents the variance (min$^2$) in the longitudinal dispersion model.

Figure 7:
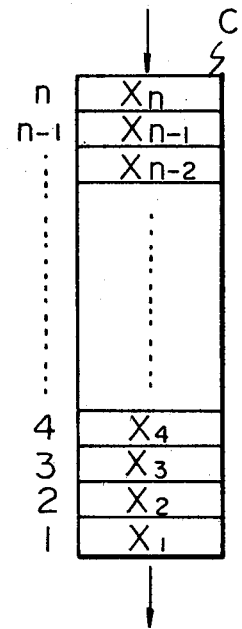

FIG. 7 illustrates an example of an adsorption column in which a classified packing is packed in the form of layers in the order of average particle size according to the present invention. In FIG. 7, C represents an adsorption column, 1 through n indicate numbers of layers of the packing classified, and $X_1$ through $X_n$ represent the average particle size of the layers 1 through n, respectively. The relation of $X_n > X_{n-1} \ldots X_3 > X_2 > X_1$ or $X_n < X_{n-1} \ldots X_3 < X_2 < X_1$ is established. The arrow indicates the flow direction.

According to the present invention, a uniform packed layer necessary for an adsorption column can be obtained by a method in which the ratio of the inner diameter of the column to the average particle size of a packing to be packed in the column is adjusted to at least 20, the packing is classified to fractions having a narrow classification latitude suitable for the required uniformity and the fractions of the packing are packed in the form of layers in the order of particle size. The classification latitude of each filler fraction may be determined according to the required uniformity, but a narrower latitude is ordinarily preferred and in view of the classifying technique and cost, it is especially preferred that the classification latitude of each fraction be within 10% of the average particle size of the packing before the classification. When the packing is packed in the form of layers of fractions, if the particle size greatly differs between adjacent layers, there occurs a phenomenon of so-called percolation in which small particles are intruded among large particles, and the packing structure is likely to be heterogeneous in the adjacent layers. Accordingly, it is preferred that the difference of the particle size between adjacent layers be as small as possible. In other words, it is necessary that the fractions of the packing should be packed in the order of particle size. In order to prevent occurrence of a so-called "percolation" during the packing step or during the adsorbing step, it is especially preferred that the fractions of the packing be packed so that fractions having a smaller particle size are located in the downstream portion of the column. This embodiment of the present invention will now be described with reference to FIG. 7.

A column C packed with solid particles is illustrated in FIG. 7. According to the present invention, a packing having a broad particle size distribution is classified in advance into fractions having a predetermined classification latitude, preferably a classification latitude within 10% of the average particle size of the packing before the classification, and layers of these fractions having an intended particle size distribution having an average particle $x_i$ ($i=1, 2, 3, \ldots, n-1, n$) are packed in sequence closely to one another in the flowing direction, preferably in increasing order of particle size from the downstream side of the column. In FIG. 7, a relation of $x_n > x_{n-1}, \ldots, x_2 > x_1$, or $x_n < x_{n-1}, \ldots, x_2 < x_1$ is established among the particle sizes $x_1, x_2, \ldots, x_{n-1}$ and $x_n$ corresponding to the fractions $1, 2, \ldots, n-1$ and $n$ of the classified packing. Incidentally, in FIG. 7, the arrow indicates the flow direction of the liquid. In the packed column shown in FIG. 7, a packing classified into fractions differing gradually and continuously in the particle size is packed in order of particle size, preferably in the increasing order of particle size in the flowing direction.

In the present invention, since the classification latitude of each fraction of the packing is very narrow, when the packing is packed in the column, a high precision as required when a packing having a broad particle size distribution is packed is not required, but it is necessary to select and adopt a method capable of providing a highest uniformity according to given conditions. For example, the above-mentioned Sock method may be adopted for packing the filler into the column in the present invention.

In order to increase the pack density and enhance the stability of the formed packed layer, there may be effectively be adopted a method in which the fractions of the filler are packed under vibration having a frequency of 0.1 to 5000 cycles per second, which is easily obtainable.

In case of a small-scale apparatus, such as a chromatographical separation apparatus for the analysis, there may be adopted a conventional vibration method in which the column is entirely vibrated or tapped. However, in case of a large-scale apparatus, it is very difficult to vibrate or tap the column entirely. Moreover, in order to obtain and maintain a uniform packing structure, it is necessary to apply vibration uniformly in the radial direction of the column. Accordingly, the above-mentioned conventional vibration method cannot be applied directly to the present invention. In short, an appropriate vibration method should be adopted according to the radius, length and weight of the column so that the pack density is increased and a stable packed layer which hardly changes with the lapse of time is formed. We found that when there is adopted a vibration method in which vibrators are inserted in the packing packed according to the above-mentioned method so that each vibrator occupies a sectional area of 0.1 to 100 cm$^2$ of the column and the packed packing is vibrated at a frequency of 0.1 to 5000 cycles per second, a satisfactory effect can be easily obtained even in the case of a large-scale apparatus. If the occupying area of each vibrator is smaller than 0.1 cm$^2$, the vibration method is practically disadvantageous because preparation of vibrators having such a small occupying area is very difficult. If the occupying area of each vibrator is larger than 100 cm$^2$, it becomes difficult to obtain a satisfactory vibrating effect uniformly throughout the packed zone and the packing structure becomes uneven in the radial direction of the column. A vibration frequency of 0.1 to 5000 cycles per second, which is ordinarily obtained by inserted vibrators, is preferred as the vibration frequency. From the viewpoint of prevention of destruction of the packing particles, it is preferred that the vibration be applied in the radial direction of the column. However, under certain working conditions, for example, the structure of the vibrators, the vibration may be applied in the axial direction of the column. The amplitude of the vibration ordinarily approximates the particle size of the packing. It is preferred that the vibration time be relatively long when the vibration frequency is low and that the vibration time be relatively short when the vibration frequency is high. It is ordinarily preferred that the vibration time be about 1 to about 5 minutes. Too long a vibration time is not preferred because segregation which results in channeling is readily caused on the contrary. The vibration time is appropriately set within the above range according to the kind of the vibrators to be used and the stability of the bed to be formed in the column.

Good results are ordinarily obtained when vibrators having a rod-like or needle-like shape are used. In the case where destruction of packing particles is likely to occur, vibrators having a disc-like shape may be used.

An embodiment of the foregoing vibration method is illustrated in FIG. 1.

Ordinarily, an adsorption column having one single-flow passage is used. However, in the case where the opening diameter becomes too large in case of a column having one single-flow passage and formation of a uniform packed layer is therefore difficult, there may effectively be used an adsorption column having a plurality of flow passages arranged in parallel. More specifically, if the sectional area for each flow passage is reduced by provision of a plurality of flow passages, the non-uniformity of the packing structure in the radial direction, which is generated at the step of packing the packing, is drastically reduced. It may be considered that increase of the number of flow passages will result in certain increase of the construction expenses, but reduction of the thickness of the wall material results in some decrease of the construction expenses. The number of the flow passages is set appropriately case by case. It is necessary that the residence time should be made equal among the respective flow passages. This control, however, is much easier than the control for attaining uniform packing in a large-diameter column. In short, it is determined according to the required separation precision and the construction expenses whether or not an adsorption column having a plurality of a flow passages should be adopted.

In the case where uniform packing is attained by a plurality of flow passages, good results are obtained when this attainment of uniform packing can be made more easily than attainment of uniform packing in case of a column having a single flow passage having a large diameter, and an especially high effect is attained when the sectional area of each flow passage is at least 0.03 m². If the sectional area of each flow passage is smaller than 0.03 m², the effect by providing a plurality of single-flow passages is not prominent. The sectional shape of each single-flow passage is not particularly critical. In view of the easiness in construction of the column and the lay-out flexibility, is preferred that each single-flow passage should have a cylindrical shape, and from the viewpoint of the compactness, it is preferred that single-flow passages be formed by partitioning the interior of a large cylinder. Examples of lay-out of a plurality of single-flow passages are shown in FIGS. 2-a through 2-i, and an appropriate lay-out may optionally be chosen.

In carrying out the above-mentioned method for realizing a uniform stream in the packed layer, means for satisfying the above-mentioned condition (B) should be adopted. If uniform distribution of the fluid to the packed zone and uniform gathering of the fluid from the packed zone cannot be attained, a uniform flow as a whole can also hardly be obtained. In the packed column of the present invention, the method for uniformalizing the distribution and gathering of the fluid should be determined while both the desired degree of the distribution and gathering of the fluid and the difficulty of attainment of this object are taken into consideration. We invented the method described below, which can satisfy both of the above requirements and can be applied not only to a column having one flow-passage having a large diameter but also to a column having a plurality of flow-passages. More specifically, according to the present invention, there is provided a method in which, in order to supply a fluid to the above-mentioned packed column or discharging the fluid therefrom, there is formed a flow passage in which the confluent junction is branched by repeating division of the junction into 2 to 4 branches, so that the respective branches are substantially equal to one another in the entire length, the entire volume, the number of bends, the angles of the bends and the shapes of the bends and the final branch ends of the flow passage adjacent to the packed zone are uniformly distributed with substantially equal sectional areas with respect to the radial direction of the packed zone.

Formation of the branches of the flow passage can easily be attained by, so to speak, "tournament-shape" construction in which, as shown in FIGS. 3-a and 3-b, conduits are used as the branch passages, and 2 to 4 branches are formed from the dispersing hole and the respective junctions are divided into 2 to 4 branches. This tournament-shape construction may be three-dimensional as shown in FIG. 3-a, or all the branches are arranged on one plane as shown in FIG. 3-b. Any method can optionally be adopted according to the intended object. The method shown in FIG. 3-b is compact and is advantageous in that the space for arrangement of the branches can be reduced. In contrast, the method shown in FIG. 3-a is advantageous in that even if increase of the number of branching stages is desired, this can readily be done by increasing the number of branching stages in the longitudinal direction and a large area can be covered by forming 3 or 4 branches from one junction.

When the joining of two branches is repeated, there may be formed a tournament-shape groove flow passage on one plane plate on which a dispersion hole and a joining portion is formed as shown in FIG. 3-d. The groove may be constructed by combining three boards as shown in FIG. 3-d or the groove may be engraved on a plate having a dispersing hole or joining hole formed thereon. In this method, the number of the final branch number is not particularly restricted when this tournament-shape type connection is fabricated. Therefore, this method is characterized in that many branches can be formed in a small arrangement space, and hence, this method is effectively utilized for scale-up of the column diameter.

Furthermore, there may be constructed a tournament-shape flow passage by forming a groove on one plane plate for each branching stage and combining these grooved plates through plates having holes in a number corresponding to the branch number, as shown in FIG. 3-e.

Various other modifications may be considered for constructing the tournament-shape flow passage, and in each case, the distributing or joining effect can be attained at the final branching stage and an appropriate method can optionally be chosen according to the manufacturing technique and the arrangement space.

When the number of the branching stages is restricted, it sometimes becomes necessary to form five or more branches from one joint in some stage. Whether the number of branches for each stage is adjusted to 2 to 4 while reducing the number of the branching stages or at least 5 branches are formed in some stage is determined while increase of the difficulty in the machining operation owing to increase of the branches at some stage and deviation from the uniform distributing or gathering to or from the packed zone owing to reduction of the number of the branching stages are duly taken into consideration. At any rate, increase of the number of branches to 5 or more in some branching stage is included in the scope of the present invention. The number of branches from one junction may optionally be chosen in the range of from 2 to 4. However, in view of the machining precision for forming equal branches, it is preferred that the number of branches be smaller.

In order to make the uniform flow from the branched flow passage present as a uniform adsorption band in the packed layer or gather the adsorption band at the outlet of the packed layer uniformly through the branched flow passage, it is indispensable that openings in the final branching stage of the branched flow passage should be uniformly formed for respective equal sectional area sections as shown in FIG. 3-c. In FIG. 3-c, there are arranged three different kinds of sections A, B and C, but these sections are substantially equal to one another in the sectional area. It is preferred that each opening be located at the controid of the corresponding section.

In order to form an adsorption band uniform in the radial direction of the column in the packed zone thereof, it is preferred that at least one opening be formed for each 0.2 m² of the sectional area of the packed zone, and it is also preferred that the number of openings formed per unit sectional area of the packed zone be larger. However, the number of openings formed per unit sectional area of the packed zone should be determined while the machining precision is taken into consideration. In order to more effectively attain the above object, there may be adopted an embodiment shown in FIG. 3-*f*, in which the openings in the final branching stage of the branched flow passage are connected to the packed zone through a member having the bottom face covering the entire surface of the packed zone, in the interior space of which beads are packed in order to prevent re-mingling (or back-mixing) by reverse flows, such as conical reducers as shown in FIG. 3-*f*.

According to the above-mentioned method, the difference of the flow speed with respect to the radial direction can be substantially eliminated in distribution and gathering of the fluid, and uniform distribution or gathering can easily be accomplished and even if the column diameter is increased for scale-up, this effect can similarly be attained with ease only by increasing the number of branches. Moreover, compact design can optionally be adopted according to need. Therefore, this method is very advantageous in various points over the conventional distributing and gathering methods.

If this distributing and gathering method is applied to the adsorption column of the present invention having a uniform packed layer according to need, the effect of prevention of channeling in the fluid can be enhanced, and even in a large-scale adsorption-separation system, the intended adsorption and separation can be performed at a very high efficiency. Therefore, according to the present invention, scale-up of the adsorption column, which has been very difficult according to the conventional techniques, can be realized without a substantial reduction in separation efficiency.

The effects of the present invention will now be described in detail with reference to, but are by no means limited to, the following Examples.

EXAMPLE 1

A granular, potassium-ion-exchange zeolite of the type Y having a particle size in the range of from $105\mu$ to $297\mu$ (hereinafter referred to as "untreated zeolite") was classified into fractions having a particle size difference latitude of 10 to $20\mu$ by a dry-type classifying machine. The obtained fractions are shown in Table 1. The degree of classification expressed by the following formula was 5 to 10%.

Degree of classification = $\dfrac{\text{latitude of particle size of packing after classification}}{\text{average particle size of packing before classification}}$

TABLE 1

| Fraction No. | Particle Size Range (μ) | Proportion (% by weight) |
|---|---|---|
| 1 | 105–110 | 2.03 |
| 2 | 110–120 | 0.16 |
| 3 | 120–130 | 0.36 |
| 4 | 130–149 | 3.30 |
| 5 | 149–160 | 2.09 |
| 6 | 160–177 | 14.43 |
| 7 | 177–190 | 2.55 |
| 8 | 190–198 | 23.92 |
| 9 | 198–210 | 0.72 |
| 10 | 210–222 | 0.23 |
| 11 | 222–233 | 10.01 |
| 12 | 233–241 | 2.19 |
| 13 | 241–250 | 22.72 |
| 14 | 250–261 | 1.99 |
| 15 | 261–273 | 1.27 |
| 16 | 273–279 | 0.75 |
| 17 | 279–289 | 7.02 |
| 18 | 289–297 | 4.26 |
| (total) | (105–297) | (100.00) |

Each fraction shown in Table 1 was heated and dehydrated for 4 hours in an electric furnace maintained at 400° C. (the heated and dehydrated zeolite is hereinafter referred to as "pre-treated zeolite").

A stainless steel column having an inner diameter of 200 mm and a length of 2.5 m, which was provided with a distributing and gathering device of the type shown in FIG. 4-*b*, in which device the end angle $\theta$ was 60°, the straight portion length a was 10 cm and glass beads having a size of 1 mm were packed, was prepared. The pre-treated zeolite comprising the fractions in proportions shown in Table 1 in a total amount of 44.0 kg were packed in the column from the top end of the flow direction in the order of increasing particle size according to the Sock method. Then, 0.2 kg of the fraction No. 18 was further packed so that the column was completely packed with the zeolite. The average pack density ($\rho_1$) was 0.563 kg/l. Then, furan was passed at a flow rate of 10 m/hr through the packed column in a down-flow manner by using a diaphragm pump to fill void portion unit furan. Then, a ball valve arranged at the outlet was closed. The inner pressure of the column was elevated to 20 kg/cm² by the above pump and the outlet ball valve was opened to reduce the pressure all at once to atmospheric pressure (this operation is hereinafter referred to as "pressure swinging"). This pressure swinging operation was repeated 100 times to remove air bubbles in the column completely. Then, a head flange was opened, and the zeolite of the fraction No. 18 was packed in an open top space formed by increase of the pack density. The amount of the zeolite additionally supplied was 0.6 kg, and the average pack density ($\rho_2$) after packing of the additional amount of the zeolite was 0.570 kg/l.

The variation of the average pack density by repeating the pressure swinging operation 100 times was calculated according to the following formula:

$$\Delta\rho = \dfrac{\rho_2 - \rho_1}{\rho_1} \times 100(\%)$$

It was found that the variation $\Delta\rho$ was 1.2%. This value $\Delta\rho$ is an index showing the stability of the packed layer. The smaller is the value $\Delta\rho$, the more stable is the packed bed.

Then, the liquid temperature was elevated to 55° C. by a heat exchanger arranged at the inlet of the column. Then, 10.9 l of a $C_8$ aromatic isomer mixture (hereinafter referred to as "mixed xylene") comprised of 45% of m-xylene (hereinafter referred to as "MX"), 20% of o-xylene (hereinafter referred to as "OX"), 20% of ethylbenzene (hereinafter referred to as "EB") and 15% of p-xylene (hereinafter referred to as "PX") was supplied at a flow rate of 10 m/hr into the above column by the above pump, and subsequently, furan was supplied as the desorbent at the same temperature and flow rate as described above. A sample which had passed through the column was collected from a sampling nozzle arranged at the outlet of the column at intervals of 30 seconds by a fraction collector. Each fraction was analyzed by a gas-chromatographical analysis device to obtain a chromatogram shown in FIG. 5 on which the change of the composition with the lapse of time was plotted. By using this chromatogram, the time point ($t_{75}$ in FIG. 5) where the purity of PX accumulated from the rear end was 75% was determined, and the recovery ratio ($R_{75}$) of the amount of PX obtained at the time point $t_{75}$ to the amount of PX contained in the mixed xylene was calculated. It was found that the recovery ratio $R_{75}$ was 89%. This recovery ratio $R_{75}$ indicates the efficiency of separation of PX from the mixed xylene. In other words, if channeling in the column is vigorous in the column, the portion of overlap of the PX and EB peaks is expanded and the value $R_{75}$ is decreased.

In order to quantitatively determine the degree of channeling in the column with ease, the pulse response measurement was carried out by using an aqueous solution containing 0.5% by weight of KCl. Since from the viewpoint of the experimental precision, it was not preferred to directly determine the pulse response in a large-diameter column, the measured value of the step response was converted to the pulse response according to the known method, for example, the method shown in Table 4.3-1 of D. M. Himmelblau et al., "Process Analysis and Simulation Determinative Systems", John Wiley and Sons (1968). At first, furan left in the column was completely replaced by water by passing water at a flow rate of 10 m/hr. Then, an aqueous solution containing 0.5% by weight of KCl was supplied stepwise at a flow rate of 10 m/hr. The response was measured by an electric conductivity meter arranged at the outlet and was converted to the pulse response according to the above-mentioned method to obtain a response curve as shown in FIG. 6, which was regarded as a normal distribution curve. From this response curve, the variance $\sigma^2$ in the axial direction in the longitudinal dispersion model was determined according to the following formula:

$$\sigma^2 = \frac{\beta^2}{8} \ (\text{min}^2)$$

wherein $\beta$ stands for the peak width (min) at the height of 1/e (in which e is the base of the natural logarithm) of the maximum peak height, as shown in FIG. 6.
It was found that the value $\sigma^2$ was 0.40 min$^2$. This value $\sigma^2$ is regarded as directly representing the degree of channeling. The larger is the value $\sigma^2$, the higher is the degree of channeling.

EXAMPLE 2

The experiment was carried out in the same manner as described in Example 1 except that the untreated zeolite was sintered and dehydrated at 400° C. for 4 hours in an electric furnace and was packed in the same column as used in Example 1 according to the Sock method. The following results were obtained.
$\rho_1 = 0.555$ kg/l
$\rho_2 = 0.575$ kg/l
$\Delta \rho = 3.6\%$
$R_{75} = 45\%$
$\sigma^2 = 0.98$ min$^2$ Since the packing was packed without being classified while the broad particle size distribution was retained, the stability of the packed bed, the efficiency of separating PX and the degree of channeling in the packed bed were inferior to those of Example 1 where the packing was classified into fractions having a narrow particle size distribution range and the fractions were packed in the form of layers.

EXAMPLE 3

Dowex IX8, an anion exchange resin having a particle size in the range of from 149 to 297$\mu$ was classified into fractions having a particle size difference latitude of 10 to 20$\mu$, as shown in Table 2. The degree of classification was 4 to 7%.

TABLE 2

| Fraction No. | Particle Size Range ($\mu$) | Proportion (% by weight) |
|---|---|---|
| 1 | 149–160 | 1.50 |
| 2 | 160–177 | 7.25 |
| 3 | 177–190 | 10.17 |
| 4 | 190–198 | 8.41 |
| 5 | 198–210 | 14.67 |
| 6 | 210–222 | 18.02 |
| 7 | 222–233 | 17.89 |
| 8 | 233–241 | 6.19 |
| 9 | 241–250 | 7.21 |
| 10 | 250–261 | 4.70 |
| 11 | 261–273 | 2.56 |
| 12 | 273–279 | 0.14 |
| 13 | 279–289 | 1.12 |
| 14 | 289–297 | 0.18 |
| (total) | (149–297) | (100.00) |

The anion exchange resin comprising the fractions in the proportions shown in Table 2 in a total amount of 44.5 kg was packed in the same column was used in Example 1 in the order of increasing particle size according to the Sock method. In order to fully pack the column with the resin, 0.4 kg of fraction No. 14 was further added into the column. The average pack density $\rho_1$ was 0.572 kg/l. The pressure swinging operation was repeated 100 times in the same manner as described in Example 1 except that water was used instead of furan used. Then, 0.5 kg of the resin was packed in an open space formed in the top. The average pack density $\rho_2$ after packing of the additional amount of the resin was 0.578 kg/l. The variation in the average pack density by repeating the pressure swinging operation 100 times was 1.0%. When the KCl pulse response was determined in the same manner as described in Example 1, it was found that the value $\sigma_2$ was 0.33 min$^2$.

EXAMPLE 4

The experiment was carried out in the same manner as described in Example 3 except that Dowex IX8 having a particle size in the range of from 149 to 297$\mu$ was directly used without classification as the anion exchange resin. The following results were obtained.
$\rho_1 = 0.573$
$\rho_2 = 0.585$
$\Delta \rho = 2.1\%$
$\sigma^2 = 0.79$ min$^2$ Since the packing was used without being classified while the broad particle size distribution was retained, the stability of the packed bed and the degree of channeling in the packed bed were inferior to those obtained in Example 3 where the packing was classified into fractions having a narrow particle size latitude and the fractions were packed in the form of layers.

The average pack density $\rho_1$ just after packing was slightly higher than in Example 3. Ordinarily, if the particle size range is broad, the packing structure is made non-uniform because of "percolation" or the like. However, even in this case, the pack density is sometimes increased under certain conditions. Therefore, the pack density per se has hardly any relation to the uniformity of the bed and cannot be a factor precisely indicating the uniformity of the bed. The stability of the bed should be evaluated based on the variation in the pack density when an external force (for example, flowing of fluid) is applied. The variation $\Delta\rho$ obtained in Example 3 according to the present invention was apparently smaller than the variation $\Delta\rho$ obtained in Example 4. Accordingly, it was confirmed that the stability of the bed in Example 3 was much higher than in Example 4.

EXAMPLE 5

A fixed bed type adsorption column of steel having an inner diameter of 1 m and a packed zone height of 2.5 m, and being provided with distributing and gathering devices having a structure as shown in FIG. 3-a, was used. In each of the distributing and gathering devices, there was fabricated a tournament-shape construction having 32 branches in the final branch stage, and being composed of steel pipes having an inner diameter of 15 mm in the first stage from the final branch ends, an inner diameter of 20 mm in the second stage, an inner diameter of 25 mm in the third stage, an inner diameter of 40 mm in the fourth stage, an inner diameter of 50 mm and an inner diameter of 80 mm in the junction, and conical reducers having steel balls 1 mm in diameter packed in the interior thereof as shown in FIG. 3-f were arranged in the connecting space between the final branch ends and the surface of the packed layer (respective sections had an equal area of 0.0245 m$^2$). The pre-treated zeolite comprising the fractions in the proportions shown in Table 1 in a total amount of 1100 kg was packed as the filler in the column according to the Sock method, and finally, 9 kg of the fraction No. 18 was additionally packed. The KCl step response test was carried out in the same manner as described in Example 1 except that the pressure swinging operation was carried out by using water instead of furan. The following results were obtained.

$\rho_1 = 0.565$ kg/l
$\rho_2 = 0.570$ kg/l
$\Delta\rho = 0.9\%$
$\sigma^2 = 0.49$ min$^2$ The stability of the bed and the degree of channeling were comparable to the results obtained in Example 1, even though the diameter of the column was increased in this Example.

EXAMPLE 6

The experiment was carried out in the same apparatus and in the same manner as described in Example 5 except that the untreated zeolite, which had been heated and dehydrated at 400° C. for 4 hours in an electric furnace, was packed according to the Sock method. The following results were obtained.

$\rho_1 = 0.563$ kg/l
$\rho_2 = 0.575$ kg/l
$\Delta\rho = 2.1\%$
$\sigma^2 = 1.85$ min$^2$ Since the packing was packed without being classified while the broad particle size range was retained, as is seen from the comparison with the results of Example 2 where the non-classified filler was used, the degradation of the capacity due to scale-up was prominent. Furthermore, the stability of the bed and the degree of channeling were remarkably inferior to those obtained in Example 5 where the classified zeolite was packed in the same column according to the present invention.

EXAMPLE 7

The KCl step response test was carried out in the same manner as described in Example 1 except that two adjacent fractions of the pre-treated zeolite, for example, fractions Nos. 1 and 2 or fractions Nos. 3 and 4, were mixed so that the classification degree for each new fraction was adjusted to 10 to 20% and the pressure swinging operation was conducted by using water instead of furan. The following results were obtained.

$\rho_1 = 0.562$ kg/l
$\rho_2 = 0.570$ kg/l
$\Delta\rho = 14\%$
$\sigma^2 = 0.52$ min$^2$ Since degree of the classification in the case of one layer was lessened and the particle size distribution latitude was increased, the results obtained in this Example were slightly inferior to those obtained in Example 1, but the capacity was enhanced over the capacity obtained in Example 2 where the non-classified zeolite was packed.

EXAMPLE 8

The KCl step response test was carried out in the same manner as described in Example 1 except that the fractions of the pre-treated zeolite were packed from the top end of the flow direction in the order of decreasing particle size according to the Sock method. The following results were obtained.

$\rho_1 = 0.565$ kg/l
$\rho_2 = 0.573$ kg/l
$\Delta\rho = 1.4\%$
$\sigma^2 = 0.50$ min$^2$ The pack density was not so low and the stability of the bed was fair. The channeling degree was slightly inferior to that obtained in Example 1. The reason was considered to be that since particles having a smaller particle size were located on the downstream side, these small particles were percolated in particules having a larger particle size, which were located on the upstream side.

EXAMPLE 9

The KCl step response test was carried out in the same manner as described in Example 1 except that a vibrating device having a structure as shown in FIG. 1 and comprising 78 vibrators composed of a piano wire having a diameter of 1 mm and a length of 20 cm, which were inserted into the column for every 20 cm pack height according to the Sock method (if the inserted vibrators extended through the boundary between two fraction layers differing in the particle size range, the length of the vibrators was adjusted to less than 20 cm so that they did not extend through the boundary between the two adjacent layers) (the sectional area occupied by each vibrator was 4 cm$^2$ and each vibrator was arranged on the centroid) and the column was packed with the filler while the vibration was conducted at a frequency of 20 cycles per second and an amplitude of 0.2 mm for about 3 minutes in the radial direction of the column. The following results were obtained.

$\rho_1 = 0.577$ kg/l
$\rho_2 = 0.577$ kg/l
$\Delta\rho = 0\%$
$\sigma^2 = 0.31$ min$^2$ Since packing was carried out under vibration, the bed was densely packed and was highly stabilized. Furthermore, since the vibration was uniform in the radial direction of the column, the degree of channeling of the fluid was remarkably reduced.

EXAMPLE 10

The KCl step response test was carried out in the same manner as described in Example 9 except that four vibrators having a diameter of 2 mm and a length of 20 cm were inserted into the column (the sectional area occupied by each vibrator was 80 cm$^2$ and each vibrator was arranged at the centroid). The following results were obtained.

$\rho_1 = 0.573$ kg/l
$\rho_2 = 0.575$ kg/l
$\Delta\rho = 0.3\%$
$\sigma^2 = 0.33$ min$^2$

EXAMPLE 11

The KCl step response test was carried out in the same manner as described in Example 9 except that two vibrators having a diameter of 2 mm and a length of 20 cm were inserted into the column (the sectional area occupied by each vibrator was 160 cm$^2$ and each vibrator was arranged at the centroid). The following results were obtained.

$\rho_1 = 0.565$ kg/l
$\rho_2 = 0.572$ kg/l
$\Delta\rho = 1.2\%$
$\sigma^2 = 0.41$ min$^2$ It was found that when the number of the vibrators was small, the effect of vibration was not significant.

EXAMPLE 12

The KCl step response test was carried out in the same manner as described in Example 1 except that a stainless steel column having an inner diameter of 21.4 mm and a length of 2.5 m and being provided with distributing and liquid gathering discs of the type shown in FIG. 4-b, in which both the end angles $\theta$ were 60°, the straight portion length a was 1.0 cm and glass beads were packed, was used and a commercially available massage vibrator was arranged so as to vibrate the outer wall of the column while packing was being carried out. Incidentally, the amount of the initially supplied pre-treated zeolite was 500 g and the amount of the additionally supplied fraction was 22 g. The following results were obtained.

$\rho_1 = 0.580$ kg/l
$\rho_2 = 0.580$ kg/l
$\Delta\rho = 0\%$
$\sigma^2 = 0.29$ min$^2$ It was found that when a column having a small diameter was used, it was possible to vibrate the entire column and a high effect could be obtained by this entire vibration. It was found that the method shown in Example 9, in which vibrators were inserted in the column having a diameter of 200 mm, were most effective for minimizing the influence by scale-up.

EXAMPLE 13

Twenty four stainless steel columns having an inner diameter of 200 mm and a length of 2.5 m, which were packed with the packing in the same manner as described in Example 1, were arranged in two rows as shown in FIG. 2-i, and the nozzles of distributing and liquid gathering discs of the respective columns were connected to a tournament-shape type pipe construction as shown in FIG. 3-a (the total sectional area was 0.75 m$^2$, which corresponded to an inner diameter of 970 mm), in which the first stage close to the column had two branch pipes 15 mm in inner diameter, the second stage had two branch pipes 20 mm in inner diameter, the third stage had two branch pipes 25 mm in inner diameter, the fourth stage had three branch pipes 40 mm in inner diameter and the junction had a pipe 80 mm in inner diameter, and in which the respective branch flow passages were equal in the distances to the final branch end and the junction and the number and angle of bends. The KCl step response test was carried out in the same manner as described in Example 1 except that all the columns were subjected to the pressure swinging operation in which water was used. The following results were obtained.

$\rho_1 = 0.563$ kg/l
$\rho_2 = 0.569$ kg/l
$\Delta\rho = 1.1\%$
$\sigma^2 = 0.41$ min$^2$ When the above results are compared with the results of Example 5 in which a column having an inner diameter of 1000 mm and having substantially the same sectional area as the total sectional area in this Example was used, it is seen that the degree of channeling was further reduced in this Example to a level comparable to that attained by a single flow-passage column having an inner diameter of 200 mm in Example 1, and the stability of the bed was substantially equal.

From the foregoing results, it is seen that the provision of a plurality of flow passages will be very effective for scale-up of the adsorption column by increase of the column diameter if distribution and gathering are conducted uniformly in the respective flow passages.

EXAMPLE 14

The interior of a column of steel having an inner diameter of 1000 mm and a length of 2.5 m was partitioned as shown in FIG. 2-b, and the pre-treated zeolite was packed in each flow passage in the same manner as described in Example 1. Incidentally, in each flow passage, 135 kg of the pre-treated zeolite was initially packed and 5 to 7 kg of the fraction No. 18 was additionally supplied according to the actual volume of each flow passage. The distributing and liquid gathering discs as shown in FIG. 3-a were attached to the column assembly. In each of the distributing and liquid gathering discs, two branches 25 mm in inner diameter were formed in the first stage close to the column, two branches 40 mm in inner diameter were formed in the second stage, two branches 50 mm in inner diameter were formed in the third stage and the junction had an inner diameter of 80 mm. The distances from the final branch end and junction and the number and angle of bends were made equal in the respective branch passages. Then, the KCl step response test was carried out in the same manner as described in Example 1 except that the pressure swinging operation was repeated by using water instead of furan. The following results were obtained.

$\rho_1 = 0.562$ kg/l
$\rho_2 = 0.569$ kg/l
$\Delta\rho = 1.2\%$
$\sigma^2 = 0.43$ min$^2$ It was found that a high effect could be obtained whether a plurality of flow passages were formed according to the method of Example 13 or to the method of Example 14.

EXAMPLE 15

The dispersing and liquid gathering discs of the adsorption column which had been used for the test in Example 5 were replaced by new distributing and liquid gathering discs having a structure shown in FIG. 3-d, in which tournament type branches were formed on the same plane. More specifically, each of the new distributing and liquid gathering discs consisted of a stainless steel member B shown in FIG. 3-d having a thickness of 50 mm, on which branches were engraved so that the final branch number was 64, the width of the branches closest to the junction was 50 mm and the width of other branches was 25 mm, a stainless steel member A in FIG. 3-d having a thickness of 50 mm, at the center of which a hole having a diameter of 80 mm was formed, and a stainless steel member C in FIG. 3-d having a thickness of 50 mm, on which 64 openings having a diameter of 25 mm were formed at the centroids of respective sections, these stainless steel members A, B and C being combined together as shown in FIG. 3-d. By using the above adsorption column, the KCl step response test was carried out in the same manner as described in Example 1. The value $\sigma^2$ obtained was 0.52 min$^2$. It was found that the column of this Example had substantially the same separation capacity as that of the column of Example 5.

EXAMPLE 16

For the column having the same packed zone as that used in Examples 5 and 15, the same distributing disc as used in Example 5 was used, and a liquid gathering disc of the type shown in FIG. 4-a, in which six pipes 40 mm in inner diameter were branched from the junction and circular openings having a radius of 50 cm were formed equidistantly from the center of the packed layer was used. By using this adsorption column, the KCl step response test was carried out in the same manner as described in Example 5. The value $\sigma^2$ obtained was 0.68 min$^2$. Since the liquid gathering uniformity by the liquid gathering disc used in this Example was lower than that attained in Example 5, the degree of channeling in this Example was higher than that in Example 5. However, when the results of this Example were compared with the results of Example 6 in which the non-classified zeolite was used, it was found that the degree of channeling due to the non-uniform gathering was much lower than the degree of channeling due to the non-uniform packing in the packed zone.

EXAMPLE 17

The KCl step response test was carried out in the same manner as described in Example 16 except that the distributing disc used in Example 16 was replaced by the liquid gathering disc used in Example 16 and the liquid gathering disc used in Example 16 was replaced by the distributing disc used in Example 16. The value $\sigma^2$ obtained was 0.72 min$^2$. The distributing uniformity of the distributing disc was lower than that attained in Example 5. However, as compared with the degree of channeling obtained in Example 6 in which the non-classified zeolite was used, the influence of the total disturbance on the value $\sigma^2$ was much lower in this Example.

EXAMPLE 18

The KCl step response test was carried out in the same manner as described in Example 16 except that the distributing disc used in Example 16 was replaced by the liquid gathering disc used in Example 16. The value $\sigma^2$ obtained was 1.23 min$^2$. Since both the distributing uniformity and the liquid gathering uniformity were low, the degree of channeling was increased in this Example. However, this increase in the degree of channeling was much smaller than the increase in the degree of channeling caused by the use of the non-classified zeolite.

EXAMPLE 19

The same adsorption column as used in Example 13, in which each single-flow passage was provided with the same distributing and liquid gathering discs as used in Example 13, was packed with the pre-treated zeolite under vibration in the same manner as described in Example 9. The value $\rho_1$ was 0.576 kg/l, the value $\rho_2$ was 0.576 kg/l and the value $\Delta\rho$ was 0%. Each single-flow passage was subjected to the pressure swinging operation in the same manner as described in Example 1, and the PX separating capacity was measured in the same manner as described in Example 1 except that 262 l of the mixed xylene was supplied. The value R75 was 85%. The KCl step response test was carried out in the same manner as described in Example 1. The value $\sigma^2$ obtained was 0.36 min$^2$.

This example illustrates a best mode of the scale-up of the adsorption column (the total sectional area of the column is 0.75 m$^2$).

The contents of the foregoing Examples are summarized in Table 3.

TABLE 3

| Example No. | Packing | Column Type | Number of Packed Layers | Classification Degree in Single Layer | Layer Arrangement downstream | Layer Arrangement upstream | Vibration | Number of Vibrators | Single Flow-Passage inner diameter (mm) | Single Flow-Passage sectional area (m²) | Dispersing-Gathering Type dispersing | Dispersing-Gathering Type gathering | Average Pack Density $\rho_1$ (kg/l) | Average Pack Density $\rho_2$ (kg/l) | $\Delta\rho$ (%) | PX Separation Capacity R75 (%) | Variance (min²) in KCl Pulse Response |
|---|---|---|---|---|---|---|---|---|---|---|---|---|---|---|---|---|---|
| 1 | Zeolite Y 105–297μ | single flow-passage column 200 mm × 2.5 m | 18 | 5–10% | small particles | large particles | not vibrated | — | 200 | 0.031 | 4-b | 4-b | 0.563 | 0.570 | 1.2 | 89 | 0.40 |
| 2 | Zeolite Y 105–297μ | single flow-passage column 200 mm × 2.5 m | 1 | 89% | — | — | not vibrated | — | " | " | " | " | 0.555 | 0.575 | 3.6 | 45 | 0.98 |
| 3 | DOWEX 1 × 8 149–297μ | single flow-passage column 200 mm × 2.5 m | 14 | 4–7% | small particles | large particles | not vibrated | — | " | " | " | " | 0.572 | 0.578 | 1.0 | — | 0.33 |
| 4 | DOWEX 1 × 8 149–297μ | single flow-passage column 200 mm × 2.5 m | 1 | 60% | — | — | not vibrated | — | " | " | " | " | 0.573 | 0.585 | 2.1 | — | 0.79 |
| 5 | Zeolite Y 105–297μ | single flow-passage column 1000 mm × 2.5 m | 18 | 5–10% | small particles | large particles | not vibrated | — | 1000 | 0.79 | 3-a | 3-a | 0.565 | 0.570 | 0.9 | — | 0.49 |
| 6 | Zeolite Y 105–297μ | single flow-passage column 1000 mm × 2.5 m | 1 | 89% | — | — | not vibrated | — | " | " | " | " | 0.563 | 0.575 | 2.1 | — | 1.85 |
| 7 | Zeolite Y 105–297μ | single flow-passage column 200 mm × 2.5 m | 9 | 10–20% | small particles | large particles | not vibrated | — | 200 | 0.031 | 4-b | 4-b | 0.562 | 0.570 | 1.4 | — | 0.52 |
| 8 | Zeolite Y 105–297μ | single flow-passage column 200 mm × 2.5 m | 18 | 5–10% | large particles | small particles | not vibrated | — | " | " | " | " | 0.565 | 0.573 | 1.4 | — | 0.50 |

TABLE 3-continued

| Example No. | Packing | Column Type | Number of Packed Layers | Classification Degree in Single Layer | Layer Arrangement down-stream | Layer Arrangement up-stream | Vibration | Number of Vibrators | Single Flow-Passage inner diameter (mm) | Single Flow-Passage sectional area (m$^2$) | Dispersing-Gathering Type dispersing | Dispersing-Gathering Type gathering | Average Pack Density $\rho_1$ (kg/l) | Average Pack Density $\rho_2$ (kg/l) | $\Delta\rho$ (%) | PX Separation Capacity R75 (%) | Variance (min$^2$) in KCl Pulse Response |
|---|---|---|---|---|---|---|---|---|---|---|---|---|---|---|---|---|---|
| 9 | Zeolite Y 105–297μ | single flow-passage column 200 mm × 2.5 m | 18 | 5–10% | small particles | large particles | inserted vibrators 100 cycles/sec | 4 cm$^2$/vibrator | " | " | " | " | 0.577 | 0.577 | 0 | — | 0.31 |
| 10 | Zeolite Y 105–297μ | single flow-passage column 200 mm × 2.5 m | 18 | 5–10% | small particles | large particles | inserted vibrators 100 cycles/sec | 80 cm$^2$/vibrator | " | " | " | " | 0.573 | 0.575 | 0.3 | — | 0.33 |
| 11 | Zeolite Y 105–297μ | single flow-passage column 200 mm × 2.5 m | 18 | 5–10% | small particles | large particles | inserted vibrators 100 cycles/sec | 157 cm$^2$/vibrator | " | " | " | " | 0.565 | 0.572 | 1.2 | — | 0.41 |
| 12 | Zeolite Y 105–297μ | single flow-passage column 21.4 mm × 2.5 m | 18 | 5–10% | small particles | large particles | outer wall vibrated | — | 21.4 | 3.6 | " | " | 0.580 | 0.580 | 0 | — | 0.29 |
| 13 | Zeolite Y 105–297μ | multiple flow-passage column (2-i) 200 mm × 2.5 m × 24 columns | 18 | 5–10% | small particles | large particles | not vibrated | — | 200 | 0.031 | 3-a | 3-a | 0.563 | 0.569 | 1.1 | — | 0.41 |
| 14 | Zeolite Y 105–297μ | multiple flow-passage column (2-b) 1000 mm × 2.5 m × 8 divisions | 18 | 5–10% | small particles | large particles | not vibrated | — | fan-shaped | 0.100 | " | " | 0.562 | 0.569 | 1.2 | — | 0.43 |

TABLE 3-continued

| Example No. | Packing | Column Type | Number of Packed Layers | Classification Degree in Single Layer | Layer Arrangement down-stream | Layer Arrangement up-stream | Vibration | Number of Vibrators | Single Flow-Passage inner diameter (mm) | Single Flow-Passage sectional area (m²) | Dispersing-Gathering Type dispersing | Dispersing-Gathering Type gathering | Average Pack Density $\rho_1$ (kg/l) | Average Pack Density $\rho_2$ (kg/l) | $\Delta\rho$ (%) | PX Separation Capacity R75 (%) | Variance (min²) in KCl Pulse Response |
|---|---|---|---|---|---|---|---|---|---|---|---|---|---|---|---|---|---|
| 15 | Zeolite Y 105–297μ | single flow-passage column 1000 mm × 2.5 m | 18 | 5–10% | small particles | large particles | not vibrated | — | 1000 | 0.79 | 3-d | 3-d | 0.565 | 0.570 | 0.9 | — | 0.52 |
| 16 | Zeolite Y 105–297μ | single flow-passage column 1000 mm × 2.5 m | 18 | 5–10% | small particles | large particles | not vibrated | — | " | " | 3-a | 3-a | " | " | " | — | 0.68 |
| 17 | Zeolite Y 105–297μ | single flow-passage column 1000 mm × 2.5 m | 18 | 5–10% | small particles | large particles | not vibrated | — | " | " | 4-a | 3-a | " | " | " | — | 0.72 |
| 18 | Zeolite Y 105–297μ | single flow-passage column 1000 mm × 2.5 m | 18 | 5–10% | small particles | large particles | not vibrated | — | " | " | 4-a | 4-a | " | " | " | — | 1.23 |
| 19 | Zeolite Y 105–297μ | same as in Example 13 | 18 | 5–10% | small particles | large particles | same as in Example 9 | same as in Example 9 | same as in Example 9 | same as in Example 9 | 3-a | 3-a | 0.576 | 0.576 | 0 | 85 | 0.36 |

We claim:

1. A method for obtaining a uniform stream in an adsorption column for adsorbing and separating a substance to be separated from a mixture, the adsorption column having at least one single-flow passage in which the ratio of the inner diameter of the column to the average particle size of a packing to be packed in the adsorption column is at least 20, the method comprising classifying the packing to be packed into the adsorption column so that the classification latitude of each fraction is within 10% of the average particle size of the packing before the classification, and packing the fractions of the packing into the adsorption column in the order of particle size.

2. A method according to claim 1, wherein the fractions of the packing are packed in increasing order of particle size from the downstream side of the column.

3. A method according to claim 1, wherein the fractions of the packing are packed under vibration having a frequency of 0.1 to 5000 cycles per second.

4. A method according to claim 3, wherein the vibration is performed by vibrators inserted into the packing so that each vibrator occupies a sectional area of 0.1 to 100 cm$^2$ of the column.

5. A method according to claim 1, wherein the adsorption column has one single-flow passage alone.

6. A method according to claim 1, wherein the adsorption column has at least two single-flow passages, which are arranged in parallel.

7. A method according to claim 6, wherein each single-flow passage has a cylindrical shape.

8. A method according to claim 6, wherein the single-flow passages are formed by partitioning the interior of the adsorption column.

9. A method according to claim 1, wherein, in at least one of the fluid introducing zone and the fluid discharging zone, the adsorption column has a flow passage in which the confluent junction is branched by repeating division of the junction into 2 to 4 branches in principle, so that the respective branches are substantially equal to one another in the entire length, the entire volume, the number of bends, the angles of the bends and the shapes of the bends and the final branch ends of the flow passage adjacent to the packed zone are uniformly distributed with substantially equal sectional areas with respect to the radial direction of the packed zone.

10. A method according to claim 9, wherein, in each of the fluid introducing zone and the fluid discharging zone, the adsorption column has a flow passage in which the confluent junction is branched.

11. A method for obtaining a uniform stream in an adsorption column for adsorbing and separating p-xylene from a mixture of xylene isomers, the adsorption column having at least one single-flow passage in which the ratio of the inner diameter of the column to the average particle size of a zeolite packing is at least 20, the method comprising classifying the zeolite packing to be packed into the adsorption column so that the classification latitude of each fraction is within 10% of the average particle size of the zeolite packing before classification, and packing the fractions of the zeolite packing into the adsorption column in the order of particle size.

* * * * *